United States Patent

Sakamoto et al.

[11] Patent Number: 6,039,695
[45] Date of Patent: Mar. 21, 2000

[54] PROBE COUPLER FOR ULTRASOUND EXAMINATION SYSTEM

[75] Inventors: Toshio Sakamoto; Toshizumi Tanaka; Hiromu Itoi; Masatoshi Yoshihara, all of Omiya, Japan

[73] Assignee: Fuji Photo Optical Co., Ltd., Omiya, Japan

[21] Appl. No.: 09/111,794

[22] Filed: Jul. 8, 1998

[30] Foreign Application Priority Data

Jul. 24, 1997 [JP] Japan ................................. 9-212716

[51] Int. Cl.[7] ...................................................... A61B 8/12
[52] U.S. Cl. ............................................. 600/459; 600/462
[58] Field of Search ................................... 600/459, 445, 600/462, 104, 127, 137, 149

[56] References Cited

U.S. PATENT DOCUMENTS

| | | | |
|---|---|---|---|
| 4,034,744 | 7/1977 | Goldberg | 600/445 |
| 4,370,662 | 1/1983 | Hou et al. | 347/75 |
| 5,044,788 | 9/1991 | Dias et al. | 600/459 |
| 5,465,724 | 11/1995 | Silwa, Jr. et al. | 600/459 |
| 5,596,991 | 1/1997 | Tanaka | 600/462 |

*Primary Examiner*—Francis J. Jaworski
*Assistant Examiner*—Ali M. Imam
*Attorney, Agent, or Firm*—Oblon, Spivak, McClelland, Maier & Neustadt, P.C.

[57] ABSTRACT

An ultrasound probe coupler for electrically and rotationally coupling an ultrasound probe with a probe control unit of an ultrasound examination system. The probe coupler essentially includes a tail end connector provided at the tail end of a flexible cord to be connected to the probe control unit. The tail end connector is provided with a stationary ring which is fixedly connected to a tail end portion of the flexible cord, and a rotational coupler having a series of rotary rings, including at least one electrode ring, for coupling the flexible shaft with a rotational drive means and an electrode on the part of the probe control unit. The rotational coupler further includes a rotation transmission member detachably connected to one of the rotating electrode rings and projected radially outward of the inner periphery of the stationary ring for engagement with a rotational drive member on the part of the probe control unit.

8 Claims, 9 Drawing Sheets

PROBE COUPLER FOR ULTRASOUND EXAMINATION SYSTEM

FIELD OF THE ART

This invention relates generally to an ultrasound examination system with a radial scan type ultrasound probe, having an ultrasound scanner to be put in rotation within a body cavity to make ultrasound scans in the rotational direction, and more particularly to a probe coupler for electrically and rotationally coupling an ultrasound probe with a probe control unit, the probe coupler permitting to disassemble rotating component parts of the ultrasound probe from stationary components easily whenever necessary.

PRIOR ART

With regard to ultrasound examination systems of the sort as mentioned above, it has been known to employ an endoscopically inserting ultrasound probe, which is designed to be inserted into a body cavity through a biopsy channel or an instrument channel of an endoscope, for example, as disclosed in U.S. Pat. Nos. 4,802,487 and 5,211,176. Ultrasound examination systems of this sort are largely constituted by an ultrasound probe member, a probe control unit and an ultrasound image observation terminal. In use, an ultrasound probe member is introduced into a body cavity through a biopsy channel of an endoscope. Therefore, the ultrasound probe usually takes the shape of a thin or narrow flexible cord having a tiny ultrasound scanner assembly attached to its tip end. The probe control unit is connected to an ultrasound transducer element on the scanner assembly to control its operation. The ultrasound image observation terminal includes an ultrasound driver for supplying drive signals to the ultrasound transducer, an ultrasound signal processor for producing ultrasound images on the basis of return echo signals received through the ultrasound transducer, and a monitor screen for displaying the produced ultrasound images.

For easy placement in a biopsy or instrument channel of an endoscope, ultrasound probes of this type are usually subject to severe restrictions in dimensions, especially in thickness. Therefore, it has been the general practice for ultrasound probes to employ a single-element ultrasound transducer in combination with a mechanical scan system which is geared for either radial or linear ultrasound scans. In the case of a mechanical radial scan, the ultrasound transducer needs to be put in rotation by means of a rotational drive mechanism.

The above-mentioned probe control unit is provided for the purpose of rotationally driving the ultrasound transducer from outside an endoscopic biopsy channel. In construction, the probe control unit includes a rotational drive means which is arranged to rotate at least the ultrasound transducer by remote control, in combination with a position detection means which detects the angular position of the ultrasound transducer. In addition to the rotational drive means, the probe control unit functions as signal relay means for signals to and from the ultrasound transducer and the ultrasound image observation terminal.

In an ultrasound examination using an endoscopically inserting ultrasound probe as described above, firstly an elongated insertion instrument of an endoscope is inserted into a body cavity along a canal or path of insertion. In doing so, the endoscopic insertion instrument can be easily introduced into an intracavitary region of particular interest or to a position suitable for observation of a diseased portion since an endoscopic observation system is built into a fore distal end portion of the insertion instrument. As soon as a diseased portion is spotted by an endoscopic examination, the ultrasound probe is placed in a biopsy channel of the endoscope through an opening of an entrance housing, which is provided on a head grip assembly of the endoscope, until a distal end portion of the ultrasound probe is extended out of the endoscopic insertion instrument by a predetermined extension length. In this state, ultrasound pulse signals are transmitted from the ultrasound transducer toward an intracavitary wall of interest to receive return echoes from body tissues in various tomographic regions. The received return echoes are converted into electric signals by the ultrasound transducer element, and the transmission and reception of ultrasound pulse signals is repeated at predetermined angular intervals during rotation of the ultrasound transducer element to obtain information on body tissues in the scanned range.

When an ultrasound probe is inserted into a body cavity through an endoscopic biopsy channel in this manner, the probe within a body cavity can be monitored through the endoscopic observation system and checked if it is located in an appropriate position for an ultrasound scan. Therefore, the ultrasound transducer element on the probe can be accurately and easily located in an appropriate position facing toward an intracavitary portion which needs an ultrasound scan. Besides, it becomes possible for the probe to transmit and receive ultrasound pulse signals at a position in the proximity of a diseased portion in an intracavitary wall or the like in order to ensure extremely high accuracy for an ultrasound examination or diagnosis, for example, especially in an ultrasound examination checking for a tumor which might exist immediately under mucous.

The ultrasound transducer element to be rotated by remote control is housed in an end cap of a synthetic resin material with excellent acoustic characteristics, which is fitted on an ultrasound scanner provided at the distal end of a flexible catheter-like cord member of the ultrasound probe. The flexible cord member has a flexible shaft of tightly wound coils fitted in a flexible sheathing outer tube which forms an outer skin layer of the cord member. The fore end of the flexible outer tube is connected to the end cap, while the fore end of the flexible shaft within the flexible outer tube is connected to the ultrasound transducer element. A signal cable which is passed internally of the flexible shaft is connected to the ultrasound transducer element. The proximal end of the flexible outer tube is retained in a fixed state in use, so that, when the flexible shaft is turned within the outer tube along with the signal cable, its rotation is transmitted to the ultrasound transducer element to rotate same within the end cap.

The probe control unit is provided with a rotational drive source for the ultrasound transducer, and arranged to retain the proximal end of the outer tube in a fixed state. On the other hand, the proximal end of the flexible shaft is rotatably connected to the probe control unit. Through a rotary connector which permits relative rotational movements while maintaining electrical conduction between two connected parts, the signal cable which is passed internally of the flexible shaft is detachably connected to corresponding signal lines of a cable which is disconnectibly connected to the ultrasound image observation terminal.

The ultrasound probe and the probe control unit can be provided as one and single assembly. However, according to the general practice, the ultrasound probe, which is a part to be inserted into a body cavity, is provided as a separate component and disconnectibly connected to the probe control unit. Therefore, the ultrasound probe is usually provided with a coupler or connector, which is disengageably connectible to a corresponding coupling portion on the part of the probe control unit after placing the ultrasound probe in a biopsy channel of an endoscope. When the ultrasound probe is in use, the connector on the probe remains outside the endoscopic biopsy channel and therefore its outside diameter is exempt from the dimensional restrictions as imposed by the inside diameter of the endoscopic biopsy channel. On the other hand, the flexible cord member, including the ultrasound scanner at its distal end, has to be smaller than the inside diameter of the endoscopic biopsy channel for easy passage therethrough. It follows that the ultrasound transducer element, which is housed in an end cap as mentioned above, has to be far smaller in size. Ultrasound transducer elements of small size which are high in vibration frequency and low in output power, however, have inherent problems such as a difficulty of transmitting ultrasound signals to deeper portions in patients body and weakness of return echoes which are susceptible to disturbances and deteriorations in the S/N ratio.

For the purpose of eliminating the above-described problems, one of the present inventors developed an ultrasound probe which permits the use of an ultrasound transducer element of a large size for transmission of low-frequency and high-power ultrasound pulses, as disclosed in his U.S. patent application Ser. No. 08/939,697 now U.S. Pat. No. 5,827,175. According to this prior U.S. patent application, the ultrasound probe employs a flexible cord member with a connector member at its proximal end to be disconnectibly connected to a probe control unit. The connector member is formed in a diameter which is smaller than the inside diameter of the endoscopic biopsy channel, so that the ultrasound probe can be inserted into the endoscopic biopsy channel inversely from its proximal end with the connector member through an exit opening of the biopsy channel at the distal end of the endoscopic insertion instrument. In this case, free from the dimensional restrictions imposed by the inside diameter of the endoscopic biopsy channel, the cord member may employ an end cap of a larger outside diameter to accommodate a large-size ultrasound transducer element on the ultrasound scanner assembly. Nevertheless, the invention of this prior application is not exempted from all the problems which are encountered in practical use.

The above-mentioned connector member is provided with a rigid stationary ring which is connected to the outer sheathing tube, a stationary part which is blocked against movements in the rotational direction, along with electrodes which are located on the side of the flexible shaft, a rotating part, and led out to a coupling end of the connector through the stationary ring. In use, the stationary ring is fixedly connected to the probe control unit and retained in a stationary state relative to the latter, while ultrasound signals are transmitted and received through rotating electrodes. In this regard, it is desirable for the stationary and rotating parts of the ultrasound probe to be easily separable from each other whenever necessary, for example, to facilitate troubleshooting jobs on the ultrasound probe or to permit introduction of an ultrasound transmitting medium into the entire length of the outer tube including the inner space of the end cap at the distal end of the cord member.

When coupling the ultrasound probe with the probe control unit, the electrodes are always projected on the outer side of the stationary ring. Once coupled, the electrodes have to be retained in a stabilized state by means of a stopper mechanism, which prevents the electrodes from being drawn into the stationary ring. In addition, the electrodes, which also serve as rotation transmitting members, needs to be connected to a rotational drive member on the part of the probe control unit in such a manner as to prevent slips in the latter, for example, by forming the connecting ends of the electrodes in square shape. However, when a bulky end cap is used to accommodate an ultrasound transducer element of a large diameter, which is larger than the inside diameter of the outer tube, difficulties are encountered in separating and extracting the rotating part along with the connector member. Besides, separation and extraction of the flexible shaft and electrodes through the distal end of the endoscopic insertion instrument become more difficult in case the electrodes are engaged with a stopper mechanism as mentioned above and increased in strength in addition to their square profiles. Therefore, once the ultrasound probe is assembled into an operative state, it is often the case that rotating and stationary parts of the probe are not easily separable from each other, despite inconveniences in maintenance and service.

SUMMARY OF THE INVENTION

In view of the problems as described above, the present invention has as its object the provision of an ultrasound probe which, when in an operatively assembled state, can retain electrodes securely in position on the side of a rotating flexible shaft of the probe, and which permits to separate stationary and rotating parts easily from each other whenever necessary.

It is another object of the present invention to provide an ultrasound probe coupler which, when in an operatively assembled state, can couple a connector at the tail end of a cord member with a probe control unit and retain the connector in the coupled position in an extremely stabilized state.

It is still another object of the present invention to provide an ultrasound probe coupler which permits to use electrodes of high strength to ensure higher accuracy as rotation transmission members.

In accordance with the present invention, for achieving the above-stated objectives, there is provided an ultrasound probe coupler for an ultrasound probe of an ultrasound examination system having an ultrasound scanner assembly attached to a nose end of an elongated flexible cord, the ultrasound scanner assembly having an ultrasound transducer element hermetically accommodated within an end cap and the flexible cord being detachably connectible at the tail end thereof to a probe control unit thereby to remote-control rotation of the ultrasound transducer element for radial ultrasound scans, the flexible cord member being largely composed of a flexible outer tube and a flexible transmission shaft fitted in the flexible outer tube for rotation therein, the flexible outer tube having a fore end portion thereof detachably connected to the end cap of the ultrasound scanner assembly, and the flexible transmission shaft having a fore end portion thereof connected to the ultrasound transducer element to transmit rotation thereto and internally providing a passage for a signal cable to the ultrasound transducer element. According to the present invention, the probe coupler comprises a tail end connector provided at the tail end of the flexible cord for electrically and rotationally coupling the ultrasound probe with the probe control unit. The tail end connector is provided with a stationary ring which is fixedly connected to a tail end portion of the flexible cord, and a rotational coupler having a series of rotary rings, including at least one electrode ring, for coupling the flexible shaft with a rotational drive means and an electrode on the part of the probe control unit. The rotational coupler further includes a rotation transmission member detachably connected to one of the rotating electrode rings and projected radially outward of the inner periphery of the stationary ring for engagement with a rotational drive member on the part of the probe control unit.

In a preferred form of the present invention, the rotational coupler of the tail end connector comprises a number of rotary rings connected to the proximal end of said flexible transmission shaft for rotation on the inner side of and in sliding contact with the stationary ring, including a first rotary ring formed of a metallic material securely fixed to the proximal end of the flexible shaft, a second rotary ring formed of an electrically insulating material and connected to the first rotary ring, a third rotary ring formed of a conducting metallic material to serve as an electrode, and a fourth rotary ring formed of an electrically insulating material and connected to the third rotary ring, and an electrode pin fitted in the fourth rotary ring. Preferably, the rotation transmission member is constituted by a transmission pin of strong metallic material, which is removably threaded into the third rotary ring. Even if the ultrasound is provided with a bully scanner assembly at the nose end of the flexible cord to accommodate a large-size ultrasound transducer element, it can be placed in an endoscopic biopsy channel as long as the tail end connector and flexible cord portions are passage through the biopsy channel.

The above and other objects, features and advantages of the present invention will become apparent from the following particular description of the invention, taken in conjunction with the accompanying drawings which show by way of example a preferred embodiment of the invention.

DESCRIPTION OF PREFERRED EMBODIMENTS

Figure 1:
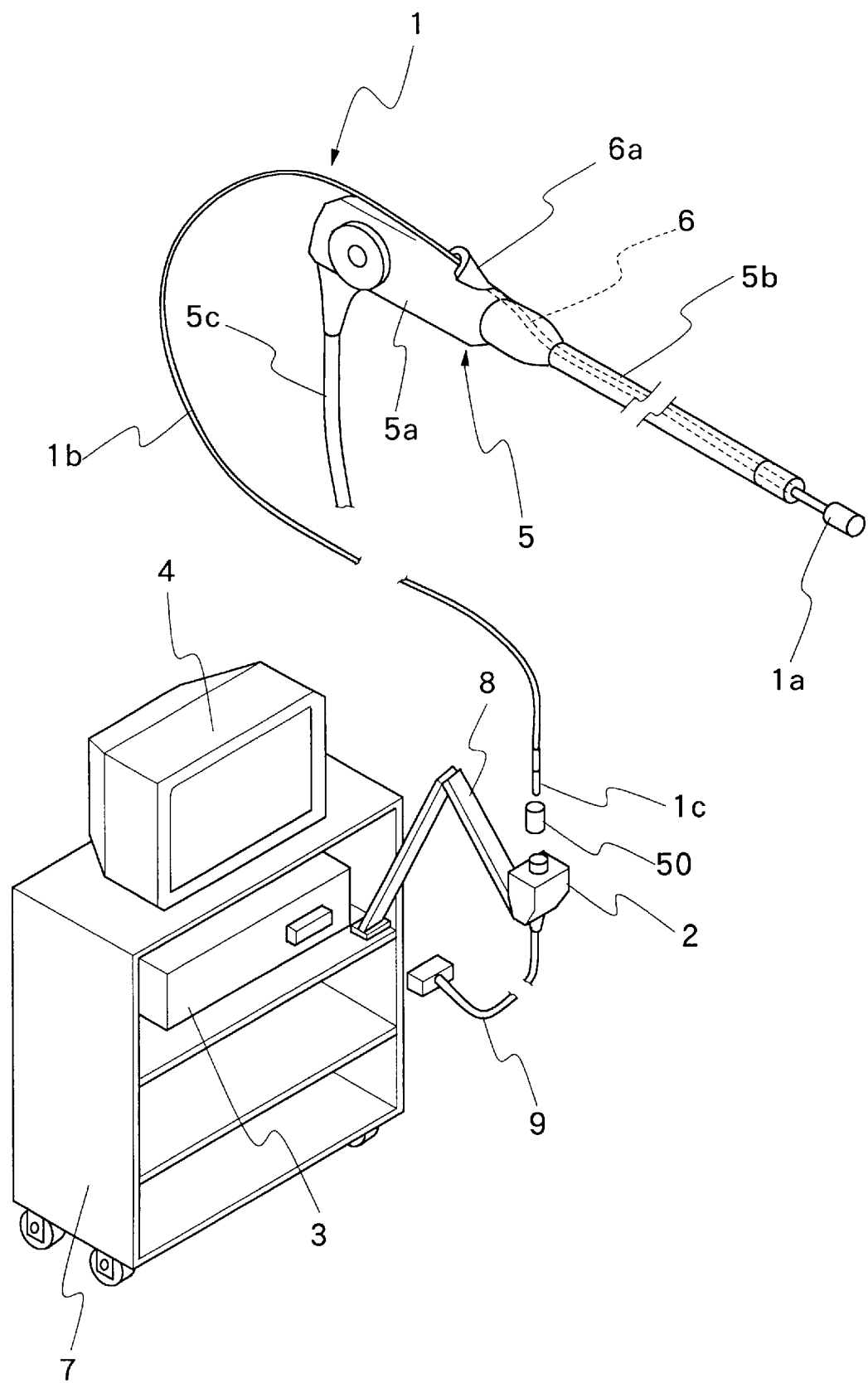
FIG. 1 schematically shows the general layout of an ultrasound examination system embodying the present invention.

Hereafter, the present invention is described more particularly by way of its preferred embodiments shown in the drawings. Referring first to FIG. 1, there is schematically shown the general layout of an ultrasound examination system incorporating an ultrasound probe coupler according to the present invention. The ultrasound examination system is largely composed of an ultrasound probe 1, a probe control unit 2 and an ultrasound image observation terminal 3 with a monitor screen 4. The ultrasound probe 1 is of the type which is introduced into a body cavity by way of an endoscope 5, more specifically, by way of a biopsy channel 6 which is provided axially and internally of an endoscopic insertion instrument 5a and accessible through an entrance housing 6a, which is provided on a manipulating head grip 5a of the endoscope 5. Led out from the manipulating head grip 5a of the endoscope 5 is a universal cable 5c to be connected to a light source and an ultrasound signal processor which are not shown in the drawings. In this instance, the ultrasound image observation terminal 3 with a monitor screen 4 is mounted on a rack 7, and the probe control unit 2 is mounted on a fore end portion of a foldable support arm 8 which is in turn connected to the rack 7 in such a way as to permit directional adjustments. A cable 9 which is led out from the probe control unit 2 is disconnectibly connected to the ultrasound image observation terminal 3.

Figure 2:
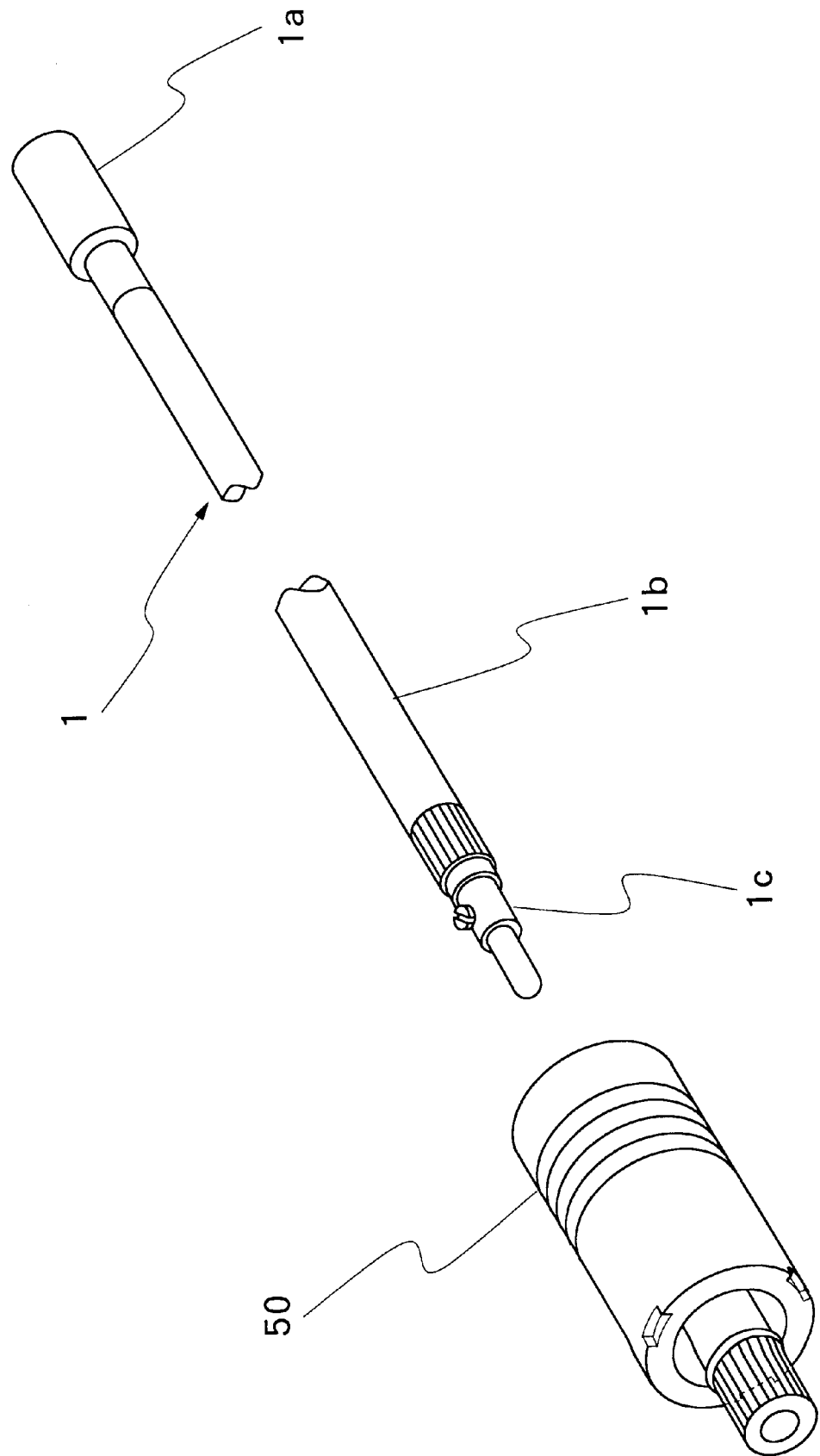
FIG. 2 is a schematic outer view of an ultrasound probe and a coupling adaptor.
Figure 3:
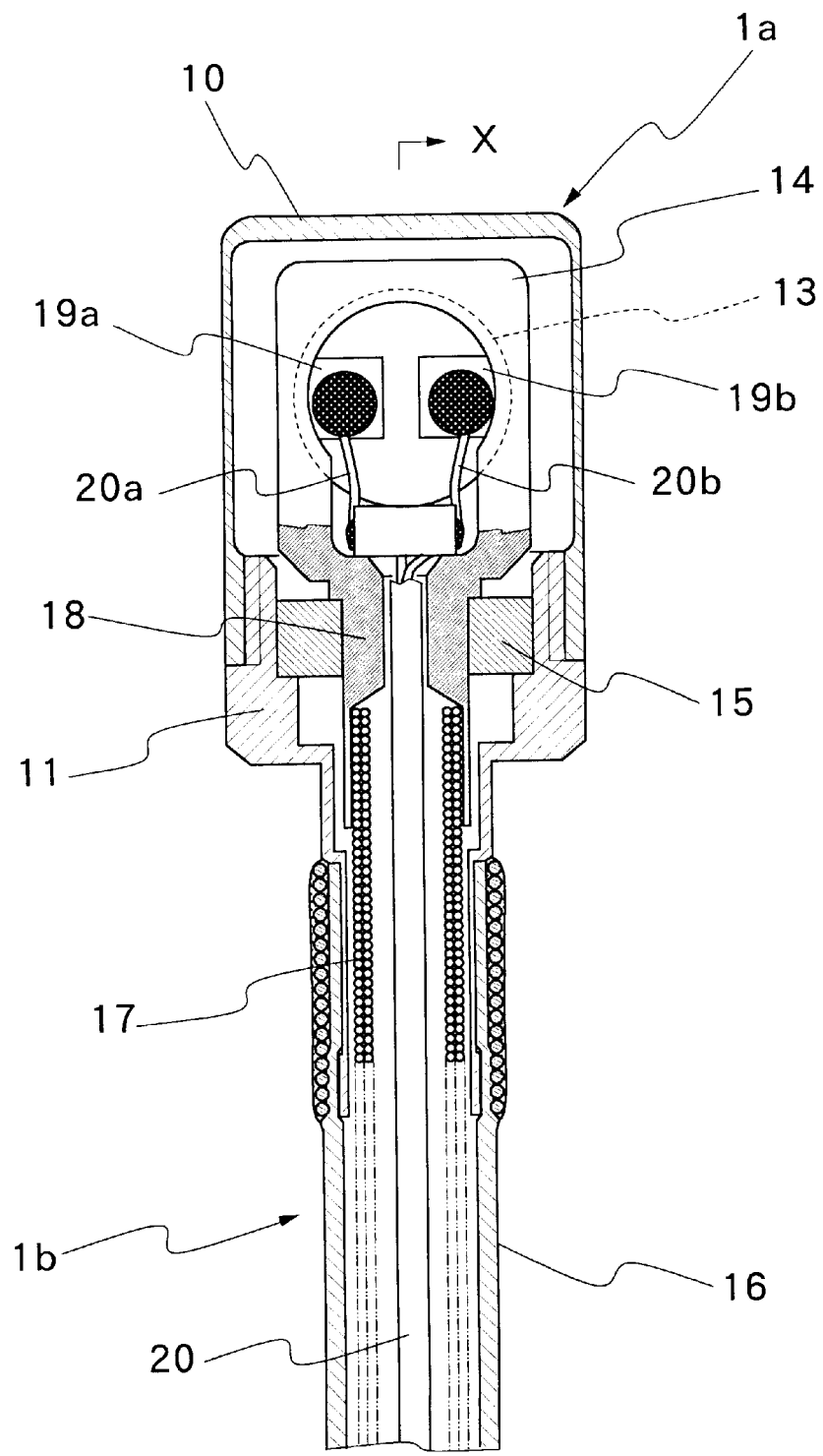
FIG. 3 is a longitudinal sectional view of a tip end portion of the ultrasound probe.
Figure 4:
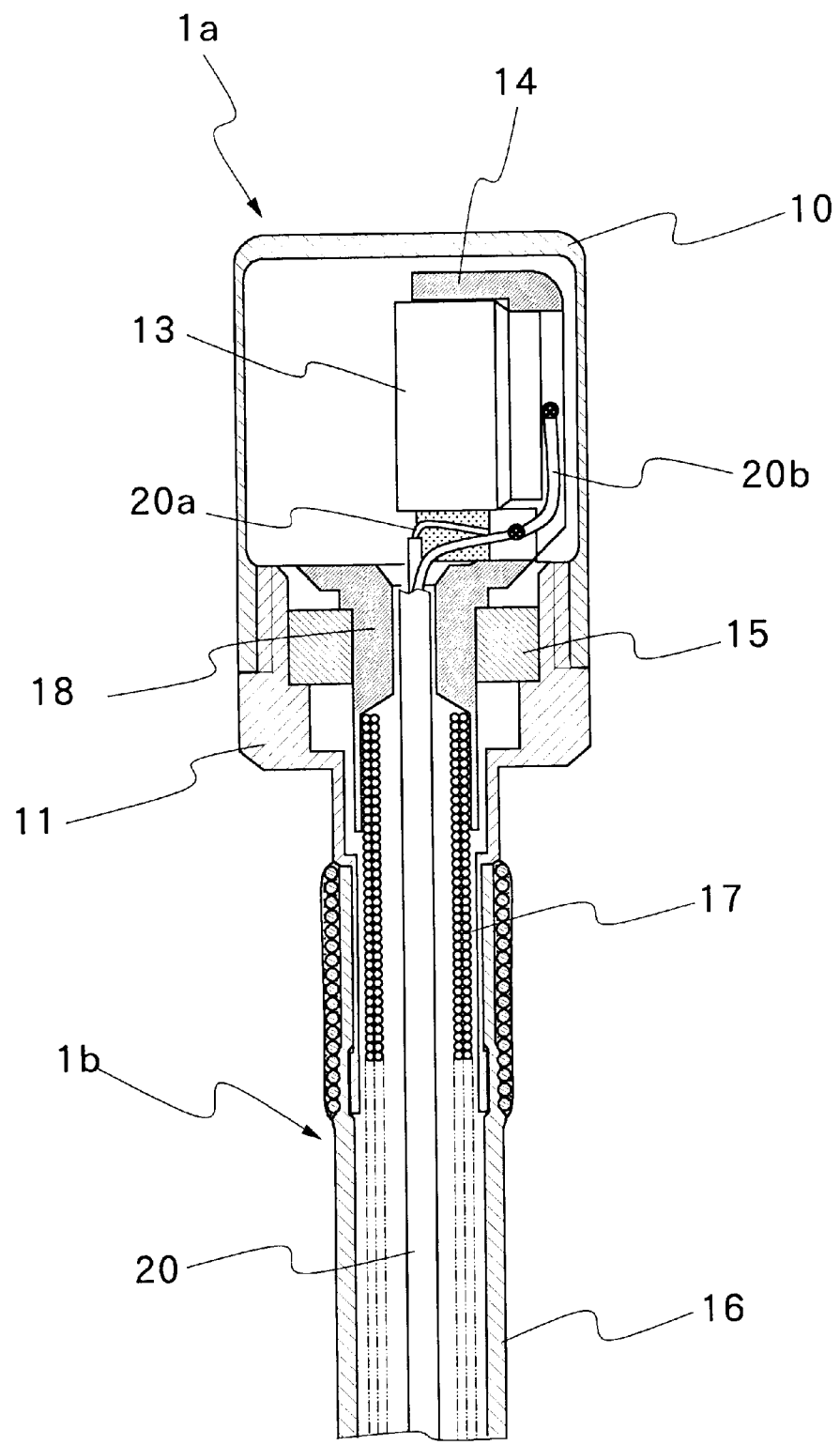
FIG. 4 is a longitudinal sectional view taken on line X—X of FIG. 3.

The ultrasound probe 1 is arranged in the construction as shown in FIGS. 2 through 5. More specifically, as seen in FIG. 2, the ultrasound probe 1 is largely constituted by an ultrasound scanner assembly 1a, a flexible cord 1b and a tail end connector 1c. As shown in FIGS. 3 and 4, the ultrasound scanner assembly 1a is provided with an end cap 10 which is threaded on a connecting member 11, encasing therein an ultrasound transducer element 13. In use, ultrasound signals are transmitted and received through the ultrasound transducer element 13 which is rotated within the end cap 10. With regard to dimensional relations of the probe components, the ultrasound scanner assembly 1a has the largest outside diameter, while the flexible cord 1b and tail connector 1 are smaller or thinner in diameter. Namely, the outside diameter of the end cap 10 which houses the ultrasound scanner assembly 1a is larger than the inside diameter of the endoscopic biopsy channel 6, while the outside diameters of the flexible cord 1b and tail connector 1c are smaller than the inside diameter of the endoscopic biopsy channel 6. The ultrasound transducer element 13 is accommodated in the end cap 10, and mounted on a rotary member 14 which is rotatably supported within the end cap 10 through a bearing 15 to scan the ultrasound transducer element 13 in the radial direction. Since the ultrasound scanner assembly 1a is larger than the inside diameter of the endoscopic biopsy channel 6, it can accommodate a large ultrasound transducer element of within a large end cap 10 for the purpose of securing a broader active surface area for transmission and reception of ultrasound signals. However, the end cap 10 is not unlimited in diameter and should have a diameter within a range which would not obstruct the view field of endoscopic observation because the ultrasound probe 1 is placed in the endoscopic insertion instrument 5b in a preparatory stage before inserting the endoscope 1 into a body cavity as will be described hereinlater.

The flexible cord 1b is constituted by a flexible outer tube 16 of soft synthetic resin material or the like and a flexible transmission shaft 17 which is fitted in the outer tube 16. Connected to the fore distal end of the outer tube 16 is the connecting member 11 which has the end cap 10 threaded thereon. The internal space of the end cap 10 is shielded from the outside when it is fitted on the connecting member 11. The flexible transmission shaft 17 is constituted, for example, by tightly wound coils, preferably, by double layers of tightly wound coils for transmitting rotations accurately in a reliable manner. The fore distal end of the flexible shaft 17 is securely fixed to a hollow neck member 18 which is connected to the rotary member 14. The ultrasound transducer element 13 is provided with a pair of electrodes 19a and 19b to connect signal lines 20a and 20b of a coaxial cable 20 which is passed through the neck member 18 and extended as far as the tail connector 1c of the probe 1 through the internal space of the flexible shaft 17.

Figure 5:
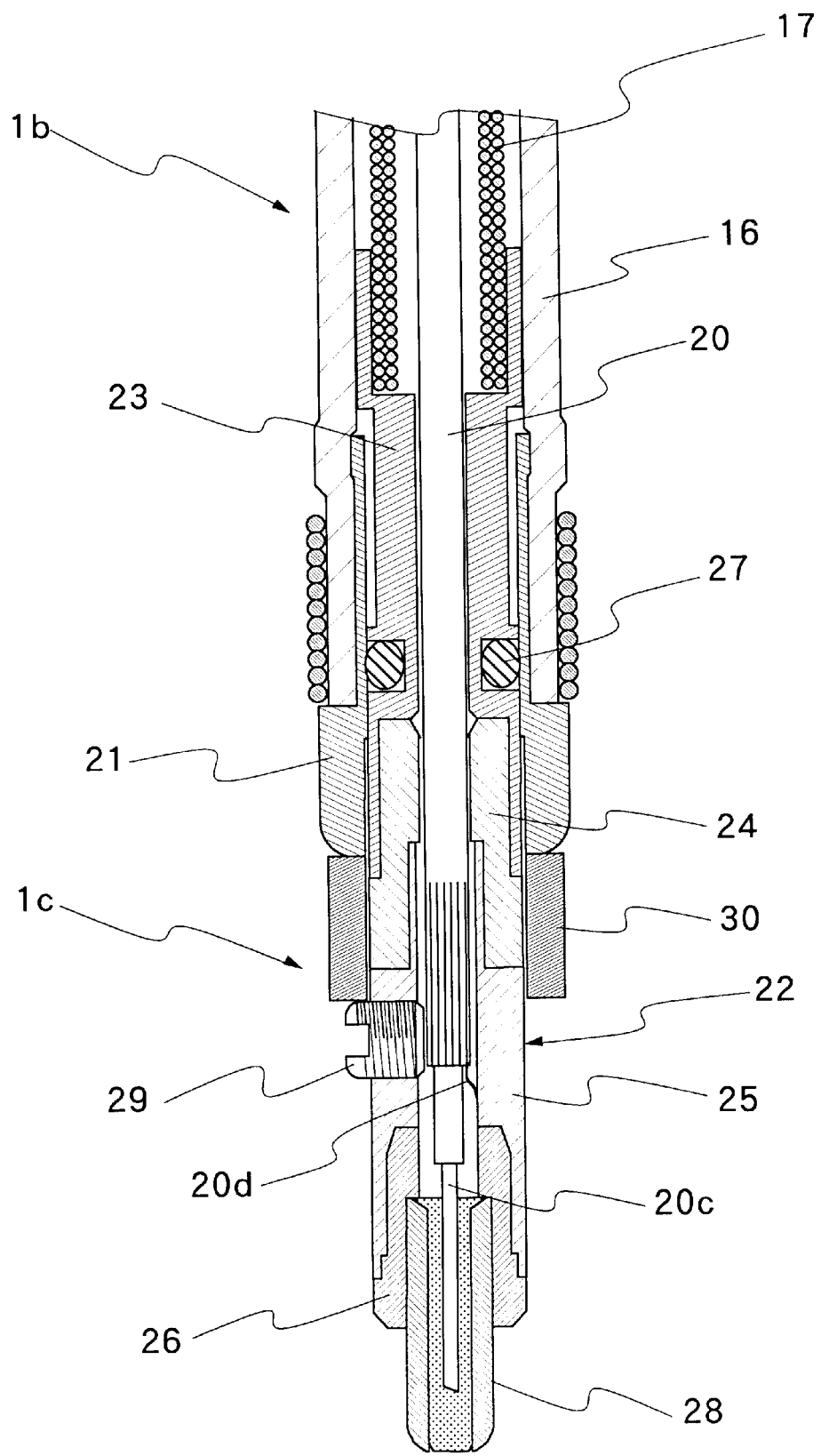
FIG. 5 is a longitudinal sectional view of a tail end portion of the ultrasound probe.

Shown on an enlarged scale in FIG. 5 is the probe construction where the proximal end of the flexible cord 1b is terminated with the tail connector 1c. More specifically, the proximal end of the outer tube 16 is fixedly fitted on a tubular retainer shell 21 of a metal which serves as a stationary ring. The proximal end of the flexible shaft 17 is connected to a rotational coupler 22 which serves also as an electrode. In this instance, the rotational coupler 22 is composed of four rotary members or rings 23 to 26 which are successively threaded one in another in the axial direction. The first rotary ring 23 which is directly connected to the flexible shaft 17 is formed of a rigid metallic material with a sufficient degree of shape retainability and received in the retainer shell 21, which is similarly formed of a rigid metallic material, for sliding rotational movements therein. A seal member 27 is fitted on the first rotary ring 23 to seal off the clearance between the first rotary ring 23 and the retainer shell 21 air- and liquid-tight. Connected to the first rotary ring 23 is a second rotary ring 24 which is formed of an electrically insulating material such as a synthetic resin material or the like. A third rotary ring 25 which is connected to the second rotary ring 24 is formed of a metal or other conducting material, while a fourth rotary member 26 which is connected to the third rotary ring 25 is formed of an electrically insulating material.

In this case, for the purpose of ensuring the sealing capacity by the seal member 27, the first rotary ring 23 is formed of a metal or metallic material. To ensure perfect sealing effects, the seal member 27 is compressed into a distorted form in a predetermined degree between the first rotary ring 23 and the retainer shell 21 which is similarly formed of a rigid metal. The third rotary ring 25 is formed of a metal because it is required to function as an electrode to be connected to the ultrasound transducer element 13. Accordingly, the second and fourth rotary members 24 and 26 of electrically insulating material are located on the front and rear sides of the third rotary ring 25. The coaxial cable 20 is passed internally through the rotational coupler 22, with its core wire 20c connected to a pin 28, which is fitted in the fourth rotary member 26, and its shield wire 20d connected to the third rotary ring 25.

Further, a rotation transmission pin 29 is removably fixed to the third rotary ring 25 by means or screw threads or other suitable fixation means. As described hereinlater, the transmission pin 29 functions to transmit rotation to the rotational coupler 22, and is arranged in such a way as to project radially outward from the outer periphery of the third rotary ring 25 by a predetermined length. A spacer ring 30 is fitted on the outer periphery of the rotational coupler 22 between the rotation transmission pin 29 and the retainer shell 21. This spacer ring 30 is abutted against the front side of the rotation transmission pin 29 and rear end face of the retainer shell 21, thereby to retain the rotational coupler 22, the flexible shaft 17 which is connected to the rotational coupler 22, the flexible tube 16 and the retainer shell 21 in an inseparably assembled state. The spacer ring 30 is formed of an electrically insulating synthetic resin material or the like with suitable slipperiness. Thus, by the spacer ring 30, the retainer shell 21 is electrically insulated from the third rotary ring 25 and the rotation transmission pin 29 which are both formed of a metallic material.

In this instance, the end cap 10 which encases the ultrasound scanner assembly 1a of the probe 1 is filled with ultrasound transmitting medium like liquid paraffin to replace air in the scanner assembly completely. Although not necessarily required, it is desirable to supply the ultrasound transmitting medium also into the tube 16 as a lubricant for ensuring smooth rotations of the flexible shaft 17. Namely, it is desirable to fill the ultrasound transmitting medium in all the internal spaces of the probe 1 from the end cap 10 to the seal member 27 at the proximal end of the outer tube 16.

Figure 6:
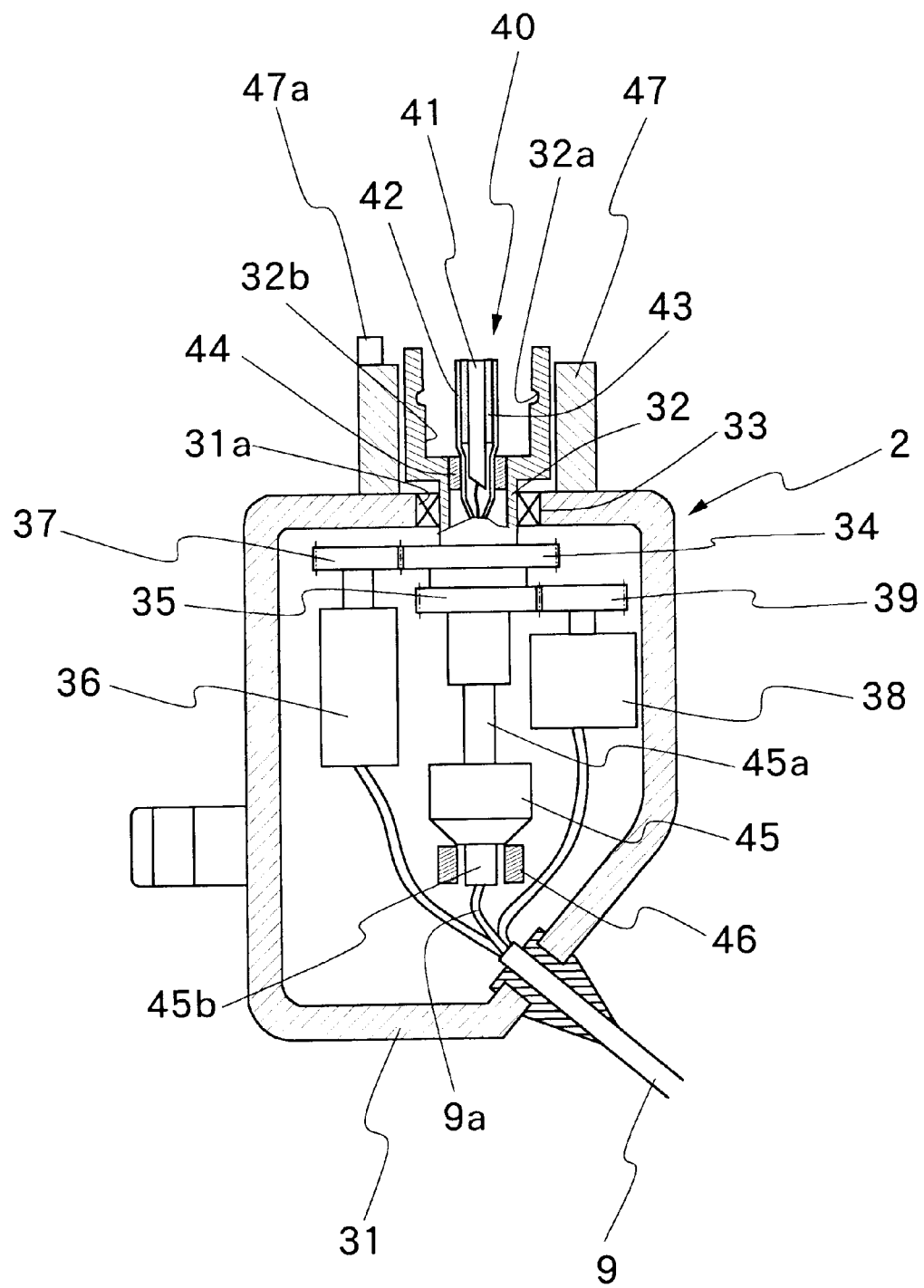
FIG. 6 is a schematic sectional view of a probe control unit.

Referring now to FIG. 6, the probe control unit 2 is provided with a casing 31 of an electrically insulating synthetic resin material or the like, in which a rotational shaft 32 is rotatably mounted through a bearing 33 to extend toward an opening 31a which is provided on the front side of the casing 31. Mounted on the rotational shaft 32 are a pair of gears 34 and 35. One gear 34 is meshed with a drive gear 37 which is mounted on an output shaft of an electric motor 36, while the other gear 35 is meshed with a follower gear 39 which is mounted on an input shaft of an encoder 38. Provided internally of the rotational shaft 32 is an electrode member 40 which is constituted by an inner pipe 41 and an outer pipe 42. These inner and outer pipes 41 and 42 are formed of an electrically conducting material and insulated from each other by an interposed insulating pipe 43. In addition, the outer pipe 42 is fitted in an insulating ring 44 which is fixedly fitted in the rotational shaft 32. Thus, by an adaptor 50 which will be described hereinlater, the core and shield wires 20c and 20d of the coaxial cable 20 are electrically connected to the inner and outer pipes 1 and 42, respectively.

One end of the rotational shaft 32 is disposed in the opening 31a on the front side of the casing 31 as mentioned hereinbefore, while the other end of the rotational shaft 32 is connected to a rotary member 45a on the rotating side of the rotary connector 45 which is provided within the casing 31. A cable 9a of the cable assembly 9 to and from the ultrasound image observation terminal is connected to a fixed member 45b on the stationary side of the rotary connector 45. The fixed member 45b of the rotary connector 45 is fitted in a rotation blocking member 46 thereby to block its rotational movements and at the same time to restrict its radial fluttering movements. A cylindrical connection housing 47 is erected around and on the outer side of the opening 31a in such a way as to circumvent the rotational shaft 32.

Figure 7:
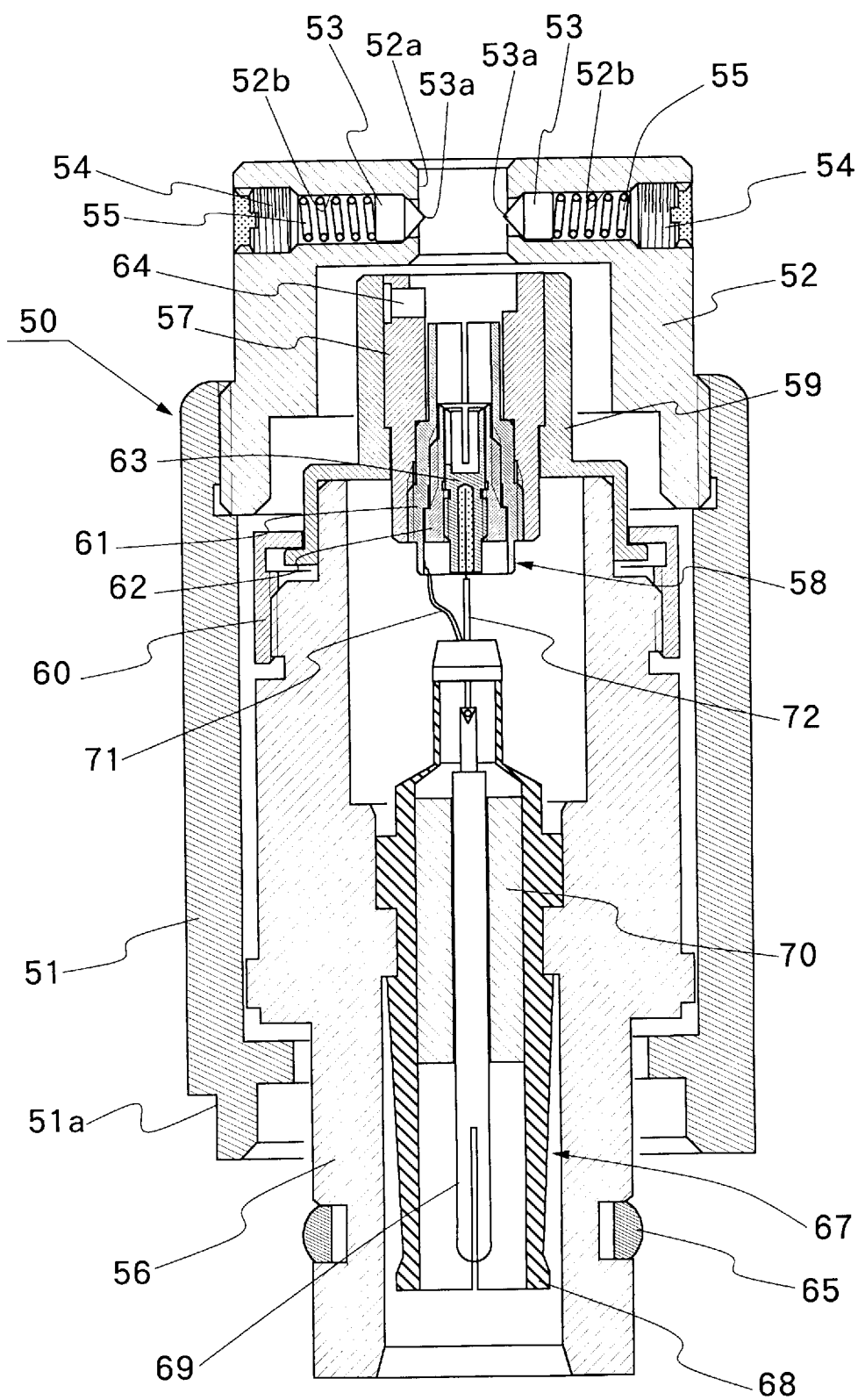
FIG. 7 is a schematic sectional view of the coupling adaptor.

The tail connector 1c of the ultrasound probe 1 is coupled with the above-described probe control unit 2 in the manner as follows. The tail connector 1c can be coupled with the probe control unit 2 either directly or through a coupling adaptor 50 as employed in this embodiment. For this purpose, the coupling adaptor 50 is provided with a first or front coupling mechanism at one end to be connected to the tail connector 1c of the probe and a second or rear coupling mechanism at the other end to be connected to the probe control unit 2. More specifically, as shown particularly in FIG. 7, the adaptor 50 is provided with stationary members including an outer housing 51 of substantially cylindrical shape and a retainer cap 52 which is threaded into one end of the outer housing 51. This stationary members of the adaptor are securely fixable relative to the casing 31 of the probe control unit 2. To this end, the outer housing 51 is provided with a stopper groove 51a which is engaged with a stopper projection 47a on the part of the connection housing 47 of the probe control unit 2 to block relative rotations of the fixed member of the adaptor 50 when connected to the latter. Further, the retainer cap 52 of the adaptor 50 is provided with an axial hole 52a to receive the retainer shell 21 of the tail end connector 1c of the probe 1. The retainer cap 52 is provided with a plural number of radial through holes 52b in its front end wall across the axial hole 52a to receive fixing screws 53, which are retractably protrudable into the axial hole 52a. More specifically, the fixing screws 53 are urged into the protruding positions by biasing springs 55 which are charged between the respective fixing screws 53 and spring seats 54. The fixing screws 53 are pointed at the respective inner ends for engagement in knurled axial grooves (not shown) which are provided on the outer peripheral surface of the retainer shell 21 of the tail end connector 1c as rotation blocking grooves. When tail end connector 1c is inserted into the axial hole 52a of the retainer cap 52 up to the retainer shell 21, the pointed ends of the fixing screws 53 are engaged with the stopper grooves to block rotations of the retainer shell 21 and the outer tube 16 of the probe 1 during radial ultrasound scans when the ultrasound transducer element 13 is rotated through the flexible shaft 17.

The coupling adaptor 50 is further provided with rotary members internally of its stationary members including the housing 51 and the retainer cap 52. Major rotary members are outer and inner rotary members 56 and 57 of generally hollow cylindrical shapes. A socket assembly 58 is threaded into the inner rotary member 57 to receive the tail end connector 1c of the ultrasound probe 1 therein. The inner rotary member 57 itself is threaded into a retainer ring 59 which is fixedly connected to the outer rotary member 56 by a box nut 60. A first tubular electrode pin 61 of the socket assembly is threaded into the inner rotary member 57, which is formed of an electrically insulating material. A tubular insulating member 62 is threaded into the first tubular electrode pin 61, and a second tubular electrode pin 63 is fitted in this tubular insulating member 62. The first and second electrode pins 61 and 63 are in the form of axially split pins with spring characteristics. Further, a radial drive pin 64 is provided on the inner rotary member 57, which drive pin 64 is abutted against the rotation transmission pin 29 on the part of the tail end connector 1c of the ultrasound probe 1 when the latter is connected to the coupling adaptor 50. By abutting engagement of the drive pin 64 with the rotation transmission pin 29, rotation is transmitted from the rotary members of the coupling adaptor 50 to the rotational coupler 22 of the tail end connector 1c.

On the other hand, a C-ring 65 is fitted on a proximal end portion of the outer rotary member 56, the C-ring 65 being engageable with an annular groove 32a around the inner periphery of a coupling portion of an increased diameter, which is provided at the outer or front end of the rotational shaft 32, for retaining the adaptor 50 securely in a connected position relative to the probe control unit 2, precluding the possibilities of its dislocations. Further, the distal end portion of the outer rotary member 56, on the proximal side of the C-ring, is formed in a spline profile for engagement in the inner periphery 32b of an outer end portion of the rotational shaft 32 which is formed in a corresponding spline profile. Indicated at 67 is a connector member which is fixedly provided within the outer rotary member 56. This connector member 67 is constituted by an outer tubular cover 68 and an electrode rod 69, each formed of an electrically conducting material. An insulating ring 70 is interposed between the outer cover 68 and the electrode rod 69 which are connected to the first and second tubular electrodes 61 and 63 through wires 71 and 72, respectively. Both of the outer cover 68 and electrode rod 69 are of an axially split tubular structure. The rotary and stationary members may be assembled through a bearing. In this particular embodiment, the housing 51 and the outer rotary member 56 are retained in small gap relation with each other.

On the other hand, in case it is desired to connect the ultrasound probe 1 directly to the probe control unit 2, the coupling portion of the probe control unit 2 is arranged substantially in the same manner as the coupling portion at the front end of the adaptor 50 on the side of the tail end connector of the probe 1.

With the probe coupler as described above, for the purpose of transmitting ultrasound signals of lower frequency and higher power, the ultrasound probe 1 can employ the large-size ultrasound transducer element 13 having a broader active surface area within the end cap 10 of on the ultrasound scanner assembly which is much larger than the inside diameter of the biopsy channel 6 of the endoscope 5. Thus, an ultrasound probe of this sort can transmit ultrasound signals with greater propulsive energy into a body under examination and improve the S/N ratio thanks to its higher reception sensitivity to echo signals. In this case, however, the ultrasound probe 1 cannot be inserted into the endoscopic biopsy channel 6 through the entrance 6a since the ultrasound scanner assembly at the nose end of the probe 1 is too bulky as compared with the inside diameter of the biopsy channel 6. Instead, the ultrasound probe 1 can be placed in the endoscopic biopsy channel 6 from the opposite direction through the exit opening at the distal end of the endoscopic insertion instrument 5b because the tail end connector 1c and the flexible cord 1b are thinner than the endoscopic biopsy channel 6.

More particularly, in a preparatory stage prior to introduction of the endoscopic insertion instrument 5b into a body cavity, the ultrasound probe 1 is placed in the biopsy channel 6 through the exit opening at the distal end of the endoscopic insertion instrument until the tail end connector 1c comes out of the biopsy channel 6 through the entrance housing 6a on the head grip 5a of the endoscope 5. In this instance, the tail end connector 1c is coupled with the ultrasound probe control unit 2 not directly but through the coupling adaptor 50, so that, the tail end connector 1c which has come out through the entrance housing 6a of the endoscopic biopsy channel 6 is connected to the coupling adaptor 50 in the first place. The connection to the adaptor 50 can be completed simply by fitting the electrode pin 28 in the axial hole 52a of the retainer shell 52. Whereupon, the electrode pin 28 is inserted in the second tubular electrode 63 of the socket 58 on the side of the coupling adaptor 50, and the rotation transmission pin 29 is brought into engagement with the drive pin 64 on the part of the coupling adaptor 50. Simultaneously, the stopper screws 53 are urged into engagement with axial grooves on the outer periphery of the retainer shell 21. As a consequence, as soon as the rotary members of the coupling adaptor 50 are put in rotation, the rotation transmission pin 29 is rotated with the drive pin 64 while the retainer shell 21 of the ultrasound probe 1 is blocked against rotational movements by engagement with the retainer cap 52 of the adaptor 50.

In assembling the ultrasound probe in this manner, one can hold with one hand the coupling connector 50 which is in a free state, so that the tail end connector 1c can be connected to the coupling adaptor 50 quite easily without possibilities of exerting strong distorting forces on the tail end connector 1c of a small diameter. Besides, the tail end connector 1c which is relatively thin and fragile is completely surrounded and protected by the coupling adaptor 50 of high strength.

Figure 8:
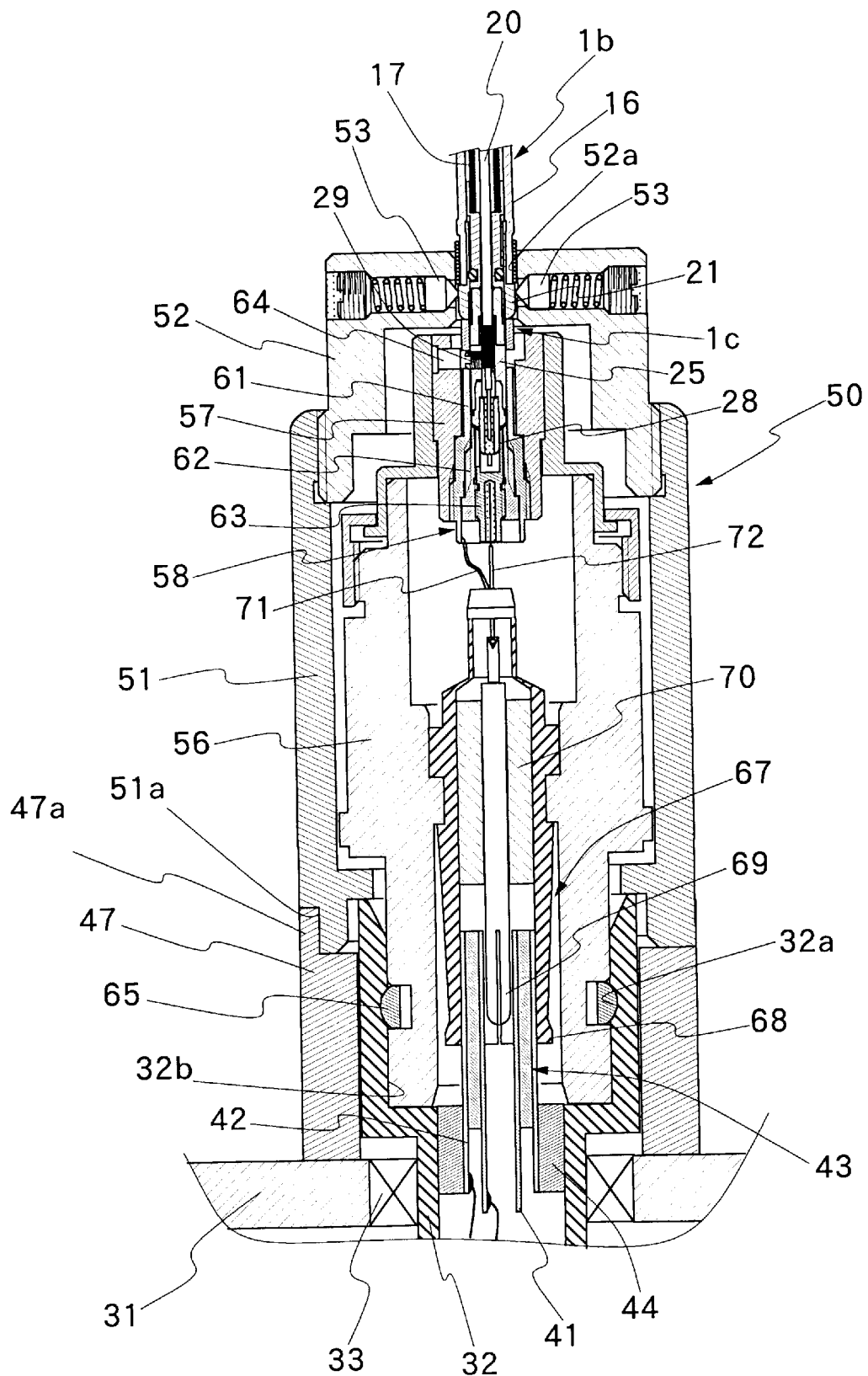
FIG. 8 is a schematic sectional view of the ultrasound probe coupled with the probe control unit through the coupling adaptor.

At the time of an ultrasound examination, the coupling adaptor 50 is connected to the probe control unit 2 as shown particularly in FIG. 8. Although the probe control unit 2 is mounted on the support arm 8 which is movable, the connector could be subjected to various forces from various directions. However, when connecting the ultrasound probe 1 to the probe control unit 2, the coupling adaptor 50 functions to protect the tail end connector 1c, which is the most fragile part of the coupling mechanism, because it is the adaptor 50 itself that is directly connected to the probe control unit 2. Upon coupling the outer rotary member 56 and housing 51 of the adaptor 50 respectively with the rotational shaft 32 and connection housing 47 on the casing 31 of the probe control unit 2, the connector member 67 is connected to the electrode member 40 on the part of the probe control unit 2. As a consequence, rotation of the rotational shaft 32 is transmitted to the rotational coupler 22 of the ultrasound probe 1 through the outer and inner rotary members 56 and 57 of the adaptor 50, and further to the flexible shaft 17 which is coupled with the rotational coupler 22. The signal lines 20a and 20b of the coaxial cable 20, which are connected to the ultrasound transducer element 13, are electrically connected to the first and second tubular electrodes 61 and 63 of the socket 58 of the adaptor 50 through the electrode pin 28 and transmission pin 29, to the inner and outer sleeves 41 and 42 of the electrode member 40 on the part of the probe control unit 2 through the wires 71 and 72 and to the ultrasound image observation terminal 3 through the rotary connector 45 and cable 9.

Accordingly, as the electric motor 36 is actuated, its rotation is transmitted through the flexible shaft 17 to the rotary member 14 at the distal end of the ultrasound probe 1 to rotate the ultrasound transducer element 13 which is mounted on the rotary member 14. Simultaneously, on the basis of angular position signals from the encoder 38, drive pules are applied to the ultrasound transducer element 13 to transmit ultrasound pulses at predetermined angular intervals, while receiving return echoes. The received return echo signals are transferred to the ultrasound image observation terminal 3 and processed to generate ultrasound images for display on the monitor screen 4. In doing so, the S/N ratio can be improved significantly thanks to the use of a large-size ultrasound transducer element 13 with a broad active surface area and high ultrasound output power. As a result, one can observe sharp and clear ultrasound images on the monitor screen 4.

In transmitting rotation from the probe control unit 2 to the flexible shaft 17 through the coupling adaptor 50 as described above, it is the rotational coupler 22, which is connected to the flexible shaft 17, that the rotation is transmitted directly from the adaptor 50. More specifically, at the rotational coupler 22 which is fitted in the retainer cylindrical shell 21 of rigid material, rotation is transmitted to the flexible shaft 17 by the transmission pin 29 which is provided outside the retainer shell 21 to couple with the drive pin 64 which is provided on the hollow rotary member 57 of the adaptor 50. Therefore, rotation can be transmitted without slips to preclude deviations of actual rotational position of the ultrasound transducer element: 13 from the position detected by the encoder 38 which is connected to the rotational shaft 32 of the probe control unit 2. Further, the transmission pin 29, which is formed of a rigid metallic material and planted on the third rotary ring 25 of a similar metallic material, is extremely high in strength to preclude damages by the rotational driving force of the drive pin 64, not to mention the third rotary ring 25 on which transmission pin 29 is planted.

Ultrasound signals are attenuated to a great degree if air intervenes between the ultrasound transducer element 13 and an opposing intracavitary wall. Therefore, it becomes necessary to supply deaerated water to a gap space between the end cap 10 and the intracavitary wall. Deaerated water is supplied either directly into a body cavity or indirectly into a balloon which is inflatable upon introduction of deaerated water. On the other hand, the end cap 10 is filled with an ultrasound transmitting medium. In this regard, it is desirable to use liquid paraffin which also has lubricative properties, and to fill liquid paraffin not only in the end cap but also in the outer tube 16 of the probe 1 for the purpose of ensuring smooth rotations of the flexible shaft 17. For this purpose, it is necessary to fill liquid paraffin in the entire inner spaces of the end cap 10 and outer tube 16 in an assembling stage of the ultrasound probe 1. Difficulties are normally encountered, however, in replacing the entire inner spaces completely with liquid paraffin as long as the flexible shaft 17 is fitted in the outer tube 16. Therefore, the ultrasound probe 1 needs to be disassembled and immersed in an ultrasound transmitting medium within a vacuum filtration vessel. Namely, after immersing disassembled parts of the ultrasound probe 1 in an ultrasound transmitting medium, the inside of the immersion vessel is maintained at vacuum pressure to let the ultrasound transmitting medium infiltrate not only into the inner spaces of the end cap 10 and outer tube 16 but into gap spaces or interstices in the flexible shaft 17 and its joint portions with the cylindrical rotary member 18 or with the rotational coupler 22.

Figure 9:
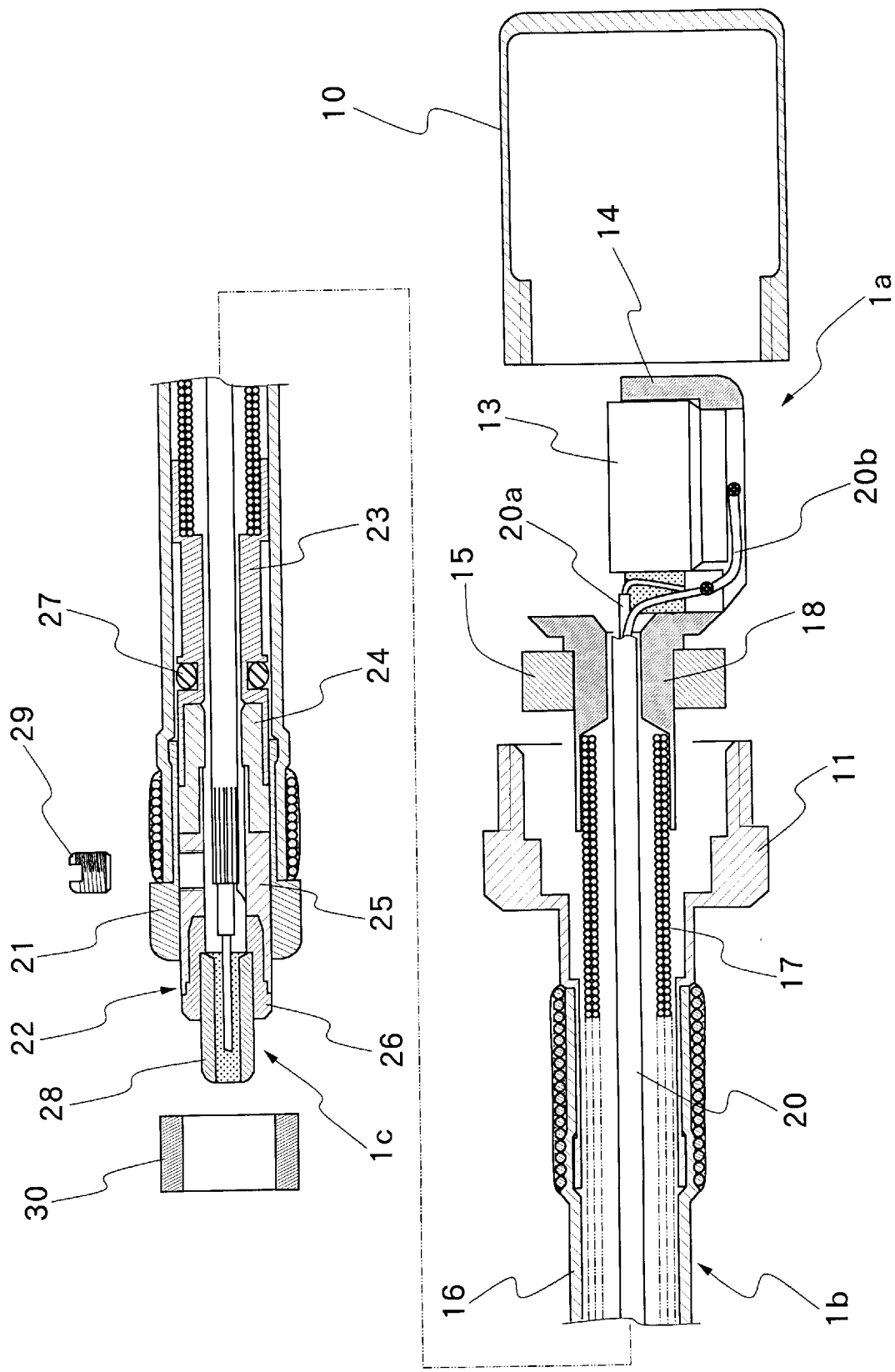
FIG. 9 is a schematic sectional view of the ultrasound probe in a disassembled state.

In order to disassemble the ultrasound probe 1, the end cap 10 is separated from the connecting member 11 in the first place as shown in FIG. 9. In the next place, the transmission pin 28 is removed from the third rotary ring 25 of the rotational coupler 22 to dismantle the spacer ring 30. In this state, the rotary member 14 is pulled out along with the ultrasound transducer element 13 to extract the flexible shaft 17 and rotational coupler 22, which are connected to the rotary member 14 out of the tube 16. Accordingly, once the end cap 10 is removed, the outer tube 16 which constitutes a major stationary part of the probe 1 can be completely separated from other rotary or rotational parts such as the rotary member 14 with the ultrasound transducer element 13, flexible shaft 17 and rotational coupler 22.

After separating the rotational and stationary parts in this manner, the ultrasound probe 1 as a whole is immersed in an ultrasound transmitting medium within a vacuum infiltration vessel thereby to infiltrate the ultrasound transmitting medium into the entire internal spaces or interstices of the respective component parts of the probe 1. After infiltration, the vessel is opened and the ultrasound probe 1 is assembled in the immersed state. More specifically, in the immersed assembling, the rotational coupler 22 of the tail end connector 1c is introduced into the outer tube 16 from the side of the connecting member 11 until it is projected out of the retainer shell 21 over a suitable length. Then, after fitting the spacer ring 30 in position, the transmission pin 29 is threaded into the third rotary ring 25, and the end cap 10 is threaded on the connecting member 11. By assembling the ultrasound probe 1 in this manner, air in the entire internal spaces or interstices of the probe can be completely replaced by the ultrasound transmitting medium. Besides, once the transmission pin 29 is mounted in position, it functions as a stopper preventing the flexible shaft 17 from moving spontaneously in the axial direction. Therefore, the flexible shaft 17 can be maintained in a suitably tensioned state for restraining spontaneous movements of the ultrasound transducer element 13 within the end cap 10 even when the flexible cord 1b is flexed into a bent form along a path of insertion.

When the ultrasound probe 1 is in the assembled state, the end cap 10 is threaded on the connecting member 11. The threaded portion can be cemented by the use of an adhesive to prevent the end cap 10 from coming off the connecting member 11. However, it is desirable for the end cap 10 to be removable to permit refilling of the ultrasound transmitting medium in the event of contamination or leakage. On such an occasion, the end cap 10 is unscrewed and removed, and then the transmission pin 29 is similarly unscrewed and removed from the third rotary ring 25 of the rotational coupler 22. At this time, the transmission pin 29 which is simply threaded into the third rotary ring 25 can be removed quite easily. Upon removal of the transmission pin 29, the flexible shaft 17 and rotational coupler 22 can be extracted out of the tube 16 by pulling out the rotary member 14 along with the ultrasound transducer element 13. For refilling the ultrasound transmitting medium, the ultrasound probe 1 is immersed in the disassembled state again in the ultrasound transmitting medium within a vacuum infiltration vessel as described above.

There may arise a necessity for disassembling the ultrasound probe 1 not only at the time of filling or refilling an ultrasound transmitting medium in the probe in a sealed state as described above but also for a repair job or for maintenance and service. In doing so, difficulties are experienced in disassembling the component parts on the rotating side, which are mostly surrounded by the component parts on the stationary side in an unaccessible manner. Therefore, in maintenance and service, for example, the rotary member 14 with the ultrasound transducer element 13 as well as the flexible shaft 17 and rotational coupler 22 or other component parts on the rotating side are easily separable from the component parts on the stationary side including the end cap 10 and outer tube 16. According to the present invention, maintenance and service for the ultrasound probe can be performed in an extremely facilitated manner, thanks to the provision of the end cap 10 which is removable from the connecting member 11, in combination with the rotational coupler 22 which is normally retained in position within the retainer shell 21 by the transmission pin 29 but can be extracted through the retainer shell 21 and the outer tube 16 upon removing the transmission pin 29.

What is claimed is:

1. An ultrasound probe coupler for an ultrasound probe of an ultrasound examination system having an ultrasound scanner assembly attached to a nose end of a flexible cord, said ultrasound scanner assembly having an ultrasound transducer element hermetically accommodated within an end cap and said flexible cord being detachably connectable at a tail end thereof to a rotational drive shaft provided on a probe control unit and serving also as an electrode on the side of said probe control unit thereby to remote-control rotation of said ultrasound transducer element for radial scans, said flexible cord member being largely composed of a flexible outer tube and a flexible transmission shaft fitted in said flexible outer tube for rotation therein, said flexible outer tube having a fore end portion thereof detachably connected to said end cap of said ultrasound scanner assembly, and said flexible transmission shaft having a fore end portion thereof connected to said ultrasound transducer element to transmit rotation thereto and internally providing a passage for a signal cable to said ultrasound transducer element, said probe coupler comprising:

a tail end connector adapted to be provided at said tail end of said flexible cord for connection to said probe control unit, said tail end connector having an electrode member adapted to be provided at a proximal end of said flexible transmission shaft and connected to said signal cable, a stationary ring adapted to be fixedly provided on a tail end portion of said flexible cord, and a rotational coupler for coupling said flexible transmission shaft with a rotational drive means on the part of said probe control unit, said rotational coupler having a rotation transmission pin detachably connected to a lateral side of a projected proximal end portion of said electrode member and projected radially outward of inner periphery of said stationary ring for engagement with a rotational drive means on the part of said probe control unit, said rotation transmission pin being adapted to block axial movements of said electrode member within said stationary ring while transmitting rotation from said rotational drive shaft on the part of said probe control unit to said electrode member.

2. An ultrasound probe coupler as defined in claim 1, wherein said electrode member is formed generally in a circular shape cross section for rotation within said stationary ring in sliding contact therewith and comprises a series of rotary rings connected to the proximal end of said flexible transmission shaft, including a first rotary ring formed of a metallic material and securely fixed to the proximal end of said flexible transmission shaft, a second rotary ring formed of an electrically insulating material and fixedly connected to said first rotary ring, a third rotary ring formed of a conducting metallic material and fixedly connected to said second ring to provide one electrode portion, and a fourth rotary ring formed of an electrically insulating material and fixedly connected to said third rotary ring, and an electrode pin fixedly connected to said fourth rotary ring to provide the other electrode portion.

3. An ultrasound probe coupler as defined in claim 2, wherein said rotation transmission pin is constituted by a pin of a conducting metallic material and detachable threaded into said third rotary ring.

4. An ultrasound probe coupler as defined in claim 2, wherein said first rotary ring is slidably fitted in said stationary ring through a seal member.

5. An ultrasound probe coupler as defined in claim 1, wherein said stationary ring on a tail end portion of said flexible outer tube is in the form of a metal ring, and a spacer ring of an electrically insulating material is fitted loosely around said rotational coupling between said stationary ring and said rotation transmission member.

6. An ultrasound probe coupler as defined in claim 5, wherein said spacer ring is of a small friction coefficient.

7. An ultrasound probe coupler as defined in claim 1, wherein said outer flexible tube and said stationary ring have an outside diameter smaller than inside diameter of a biopsy channel of an endoscope.

8. An ultrasound probe coupler as defined in claim 1, wherein said tail end connector is disconnectibly connected to said probe control unit through a coupling adaptor having signal and rotation transmission means including a drive pin member for transmitting rotation to said rotation transmission pin.

* * * * *